United States Patent [19]

Larock

[11] Patent Number: 4,814,490

[45] Date of Patent: Mar. 21, 1989

[54] ORGANOPALLADIUM APPROACHES TO PROSTAGLANDINS

[75] Inventor: Richard L. Larock, Ames, Iowa

[73] Assignee: Iowa State University Research Foundation, Inc., Ames, Iowa

[21] Appl. No.: 121,334

[22] Filed: Nov. 16, 1987

[51] Int. Cl.$^4$ ............................................. C07C 177/00
[52] U.S. Cl. ..................................... 560/120; 562/502
[58] Field of Search ......................................... 560/120

[56] References Cited

U.S. PATENT DOCUMENTS

| | | | |
|---|---|---|---|
| 3,418,102 | 12/1968 | Richter | 71/106 |
| 3,492,330 | 1/1970 | Trecker et al. | 260/453 |
| 4,113,755 | 9/1978 | Larock | 260/429 |
| 4,351,949 | 9/1982 | Larock | 548/359 |
| 4,436,934 | 3/1984 | Larock | 562/502 |
| 4,520,207 | 5/1985 | Larock | 549/79 |
| 4,563,537 | 1/1986 | Larock | 549/79 |

OTHER PUBLICATIONS

Larock et al., J. Org. Chem. 52, 1364 (1987).

*Primary Examiner*—Robert Gerstl
*Attorney, Agent, or Firm*—Zarley McKee, Thomte, Voorhees & Sease

[57] ABSTRACT

A prostaglandin precursor is made by reacting a bicyclic olefin with an alkyl (acetoxymercurio) carboxylate, a palladium salt, and an 1-alken-3-one to provide a keto ester bicycloheptane.

7 Claims, No Drawings

ORGANOPALLADIUM APPROACHES TO PROSTAGLANDINS

BACKGROUND OF THE INVENTION

The prostaglandins are an extremely important, biologically active class of C-20 unsaturated hydroxy-acids discovered first in the 1930s by Goldblatt and Von Euler in extracts of human seminal fluid and sheep vesicular glands. Due to the difficulties in isolating and determining the structures of milligram quantities of these compounds, it was not until the 1960s that their structures were determined. By then, the extreme physiological activity of these compounds was evident, and the desire for larger amounts of these valuable compounds for biological testing stimulated organic chemists to tackle the formidable problem of synthesizing these highly functionalized molecules. Within a few short years, a number of total syntheses of all of the primary prostaglandins had appeared led by the work of Professor E.J. Corey and his group at Harvard (see U. Axen, J.E. Pike and W. P. Schneider in "The Total Synthesis of Natural Products", Vol. 1, J. ApSimon, Ed., Wiley-Interscience, New York, 1973, pp. 81–142, which is incorporated herein by reference).

With the ready availability of these compounds for the first time, extensive biological testing ensued. Prostaglandins have subsequently been found to have pronounced effects on the cardiovascular and renal systems; the respiratory tract; the eye, skin, lungs, and bone; and the reproductive organs. Within the cardiovascular system alone, they apparently play a central role in regulating blood platelet aggregation, blood pressure and flow, cardiac output, heart rate, and vascular activity. While prostaglandins appear to have pharmacological potential in the treatment of asthma, nasal congestion, stomach ulcers, inflammation, hypertension, thrombosis, etc., considerable attention so far has focused on their possible use in the induction of labor, termination of pregnancy, and possible utility in contraception.

To date, the major drawbacks to clinical application of the prostaglandins have been the very broad range of physiological activity prevalent in these compounds and their brief duration of action due to rapid metabolic deactivation. The desire for longer lasting drugs exhibiting much more specific activity has recently produced a number of very interesting analogs of prostaglandins and many structure-activity studies have resulted. The interesting synthetic work of J. Fried at Chicago on oxa analogs, and recent synthesis of 8-, 12-, and 15-methyl prostaglandins which are blocked from undergoing the usual metabolic deactivation should be noted in this regard. Fried, et al., Ann. N.Y. Acad. Sci., 180, 38 (1971), incorporated herein by reference. Some of these synthetic analogs will hopefully find clinical application.

Tremendous potential also exists in the development of prostaglandin antagonists and reagents which will inhibit prostaglandin bio-synthesis and metabolism. At present, only a few prostaglandin antagonists are known. The best known and most studied are the dibenzoxazepine derivatives, especially SC-19220, phosphorylated polymers of phloretin, especially polyphloretin phosphate; and oxa- and thia-prostaglandin analogs, particularly 7-oxa-13-prostanoic acid. Considerable recent interest has also developed in potential antagonists of prostaglandin biosynthesis. In fact, it has been suggested that the biological activity of anti-inflammatory, analgesic and antipyretic drugs can be explained by the fact that they inhibit the biosynthesis of prostaglandins. It is, therefore, possible that the synthesis of specific inhibitors of prostaglandin biosynthesis and prostaglandin receptor antagonists could produce some clinically useful drugs.

For these reasons, there has been considerable work of late on the biosynthetic pathways involved in the formation of prostaglandins.

Although the natural prostaglandins show promise as potential drugs, there are a number of problems. For instance, they are metabolized very rapidly within the body. Studies on humans show that prostaglandin $E_2$, a smooth muscle contractor that is used to induce labor or terminate pregnancy, when given intravenously at 96° is deactivated in the first 90 seconds after administration. A more perplexing problem is the lack of tissue specificity of the prostaglandins. Prostaglandin $E_2$, in addition to causing uterine smooth muscle to contract to induce labor, causes gastrointestinal smooth muscle to contract, leading to cramps and diarrhea. This same compound, when aspirated into the nostrils, immediately dilates the bronchi and alleviates asthmatic attack, but at the same time, it irritates the mucous lining of the throat, causing pain and coughing.

The therapeutic potential of the prostaglandins and the lack of an abundant natural source of these compounds has led to a number of laboratory investigations to provide a total synthesis as a method of obtaining them. In addition, because of their lack of specificity in inducing pharmacological activity, it has been thought desirable to develop significant analogs of prostaglandin compounds which would be more stable than natural prostaglandins, and which would have more specificity in providing pharmacological activity.

It is an object of this invention to provide prostaglandin-like compounds which are convenient synthetic precursors for desired prostaglandins, which are thermally stable and can be prepared at good yield levels.

Yet another object of this invention is to provide prostaglandin precursors which can selectively be reacted to provide either exo or endo analogs of prostaglandins.

Yet another object of this invention is to provide a convenient and simple synthesis route for preparing precursors of prostaglandin compounds by adding an alkyl (acetoxymercurio) carboxylate to norbornene or related bicyclic olefins in the presence of a palladium salt and a 1-alken-3-one in order to produce a ketoester of a bicycloheptane.

SUMMARY OF THE INVENTION

A new synthetic route to a prostaglandin precursor employing an alkyl (acetoxymercurio) carboxylate, a palladium salt, and a 1-alken-3-one to give a ketoester of a bicycloheptane.

DETAILED DESCRIPTION OF THE INVENTION

The overall synthesis method of this invention may be represented by the following equation:

Equation 1

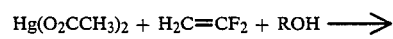

-continued $$CH_3\overset{O}{\underset{\|}{C}}-OHgCH_2\overset{O}{\underset{\|}{C}}-O-R$$

Equation 2

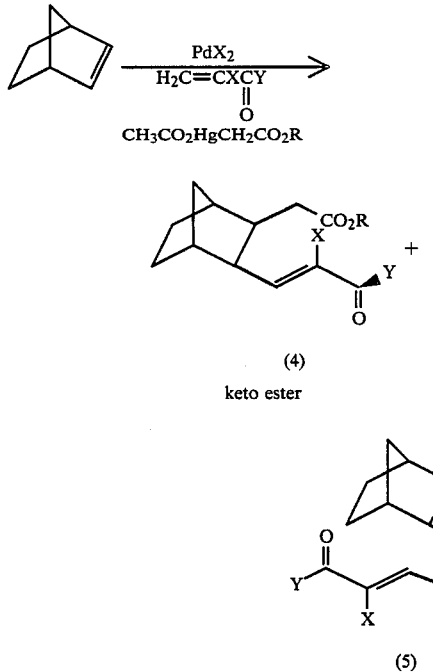

(4)

keto ester (5)

In word description, the reaction involves the production of an alkyl (acetoxymercurio) carboxylate from 1,1-difluoroethylene. This compound is then reacted with a norbornene-type compound, such as norbornene itself, as depicted in the above equation, in the presence of a palladium salt and a 1-alken-3-one. The resulting product is a keto ester of a bicycloheptane, which differs from other precursors produced by us and others in that the first side chain introduced is an ester group, and the second side chain contains a carbon-carbon double bond, whereas our previous methods introduced a carbon-carbon triple bond. Further, the reactions differ in that both side chains go into the compound in one step, as opposed to two steps.

The first reaction step, as represented in equation 1 above, is the production of an alkyl (acetoxymercurio) carboxylate from commercially available 1,1-difluoroethylene. The "R" represents a carbon chain containing 1-8 carbons. The preferred group is ethyl, but it can be any $C_1$ to $C_8$. The "R" may be any alkyl, but preferably is methyl, and the most preferred is ethyl. This process is well-known and reported in such sources as Knunyants, I.L.; Pevoca, L.Y.; Tyuleneva, U.V.; *Izv. Akad. Nauk U.S.S.R., Ser. Khim*, 1956, 844; *Bull. Acad. Sci. U.S.S.R., Div. Chem. Sci.,* 1956, 863.

The second reaction starting material is norbornene itself, substituted norbornene compounds, or a related bicyclic olefin. Norbornene is a seven-carbon bicyclic compound containing one unsaturated bond having a technical name of bicyclo[2.2.1]hept-2-ene. The dotted lines shown in the pictorial representation of norbornene in the previously presented equation represents the bonds extending below the plane of the five-member ring and can stereochemically speaking be represented in the following manner:

While norbornene is the most commonly employed starting material, it should be understood that any other bicyclic olefin may also be utilized, for example, norbornadiene and other related bicyclic olefins such as bicyclo[3.2.1]oct-6ene and bicyclo[2.2.2]oct-2-ene. Bicyclo octenes, as just described, are similar in reactivity to norbornene and differ structurally only in that they have a second carbon atom in the bicyclic bridge. Also, it should be understood that substituted norbornene compounds may be utilized successfully as a starting reactant without interferring with the basic reaction method of this invention. Of course, however, the carbon atoms of the unsaturated olefin bond of the norbornene bond must remain unsaturated in order that the addition reaction with the alkyl (acetoxymercurio) carboxylate compound, as depicted above, will occur. However, substitutions on all of the carbon moieties of the norbornene may occur. Particularly important is 7-oxabicyclo[2.2.1]hept-2-ene.

In the second reaction, the norbornene is combined with the alkyl (acetoxymercurio) carboxylate in the presence of a palladium salt and a 1-alken-3-one. The X refers to any palladium salt anion, preferably the palladium salt anion is a palladium halide salt. The most preferred salt is palladium chloride, and it is preferred that the reaction be conducted in the presence of lithium chloride. The reaction ingredient is often referred to as dilithium tetrachloropalladate having the formula:

$Li_2PdCl_4$

The reaction also occurs in the presence of a 1-alken-3-one, as represented in equation 2 above. The reference to Y or Z can be any alkyl, preferably in the range of $C_1$ to $C_{10}$. The most preferred form is 1-octen-3-one of the formula:

$H_2C=CHCOC_5H_{11}$

The reaction preferably is conducted in the presence of an organic solvent in order to provide more intimate contact between the reactants. The solvent must be a polar reaction solvent which is inert to the reaction ingredients. Suitable solvents which may be employed are tetrahydrofuran, methyl alcohol, diethyl ether, hexamethylphosphoramide, acetonitrile and the like. It is also preferred that the reaction be conducted in the presence of an excess of norbornene. By "excess", it is meant that the amount of norbornene employed be in excess of an equivalent amount. Under the most preferred embodiment, reaction of the ethyl (acetoxymercurio) acetate occurs in the presence of two equivalents of norbornene and ten equivalents of 1-octen-3-one.

The reaction is conducted in the presence of a solvent since the reactants are often solid. The reaction may be conducted at temperatures from approximately −40° C. up to room temperature or even higher with satisfactory results. In the preferred embodiment, the reaction between the norbornene, the carboxylate, the palladium salt, and the 1-alken-3-one occurs over four days at room temperature.

The prostaglandin precursor is usually a liquid and is purified by chromatography. Keto ester 4 is a diastereomeric mixture of products resulting from addition of the keto and ester side chains to opposite ends of the norbornene double bond. The "R" group is any alkyl from $C_1$ to $C_8$. The diastereomeric mixture of 4 can be separated from compound 5 by column chromatography in 40% unoptimized yield. The assignment of structure for compound 5 is based solely on mass spectral analysis and mechanistic arguments. At the end of four days, the result is an approximate 4:1 ratio of the desired keto ester (4) and the double insertion product (5) in 70% overall yield.

The construction of keto ester 4 in one step from readily available starting materials makes it a particularly valuable intermediate for the synthesis of exo-exo prostaglandin endoperoxide analogs. For example, compound 4 is readily elaborated to the endoperoxide analogs shown below by the following reaction sequence:

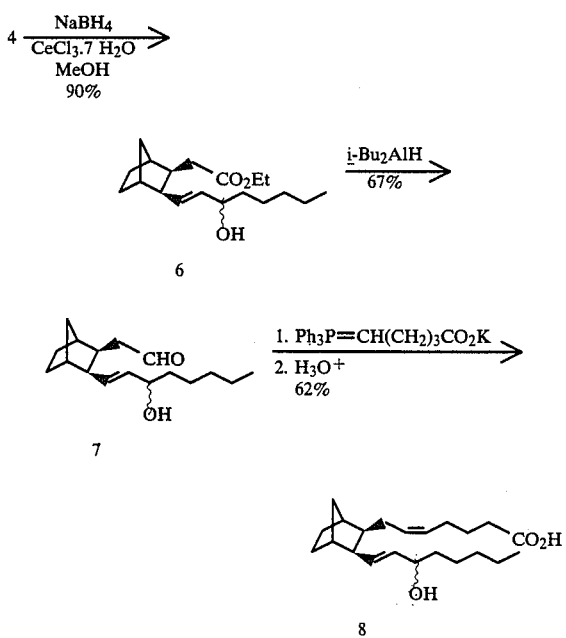

Keto ester 4 is reduced to hydroxy ester 6, and in the second step, further reduced to hydroxy aldehyde 7. Wittig olefination as described at Chapleo, C.B.; Finch, M.A.W.; Lec, T.V.; Roberts, S.M. *J. Chem. Soc. Perkin I*, 1980, 2084, produces endoperoxide analog 8. This three-step synthesis of an effective inhibitor of blood platelet aggregation proceeds in 37% unoptimized, overall yield from the readily available keto ester 4.

Another effective inhibitor of blood platelet aggregation is produced in the following scheme:

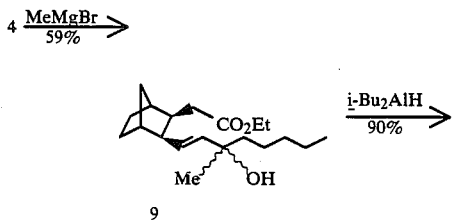

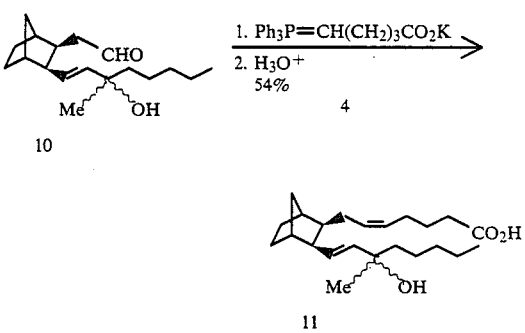

The C-15 (S) epimer of alcohol 8 has previously been reported to be an effective inhibitor of arachidonic acid and ADP-induced blood platelet aggregation. For "Organopalladium Approaches to Prostaglandins. 7. Synthesis of Prostaglandin Endoperoxide Analogs by Vinylpalladation of Norbornene" see: Larock, R.C.; Hsu, M. H.; Narayanan, K. *J. Org. Chem.*, Tetrahedron 43, 2891 (1987).

Having now described the reaction in terms of its general conditions as well as specific descriptive details for each of the reaction ingredients, the following specific examples are offered to further illustrate but not limit the process of the invention.

Synthesis of Compounds 4 and 5

Palladium chloride (0.89 g, 5 mmol) and lithium chloride(0.42 g, 10 mmol) were dissolved in 50 ml of dry tetrahydrofuran (THF). The solution was cooled to 0° C. and ethyl (acetoxymercurio) acetate (3) (1.73 g, 5 mmol), norbornene (0.94 g, 10 mmol) and 1-octen-3-one (6.3 g., 50 mmol) were added. The reaction was stirred at 0° C. for one hour and was then allowed to warm up to room temperature. After stirring for four days, the reaction was diluted with ether, filtered, washed with saturated ammonium chloride solution, and dried over $Na_2SO_4$ After removal of the solvent, the excess 1-octen-3-one was distilled under reduced pressure. Gas chromatographic mass spectral analysis of the reaction mixture showed that the desired product 4 was obtained along with compound 5 in a ratio of approximately 4:1 in a total yield of 70%. The mixture was separated by column chromatography using 4:1 hexane/ethyl acetate as the eluant. The desired product 4 was isolated in 40% yield.

Synthesis of Compound 6 and 7

A procedure generally known described at Luche, J.; Rodriquez-Hahn, L.; Crabbe, P. *J. Chem. Soc., Chem. Commun.* 1978, 601, was employed. The enone 4 (0.27 g, 0.89 mmol) and $CeCl_3.7H_2O$ (0.33 g, 0.89 mmol) were dissolved in methanol 2.25 ml). Sodium borohydride (0.034 g, 0.89 mmol) was added and the reaction mixture was stirred for five minutes. It was then diluted with ether and water and the ether layer was separated. The aqueous layer was extracted with ether, dried over $Na_2SO_4$ and evaporated to give 0.247 g (90% yield) of crude hydroxy ester 6 which was immediately reduced further.

The hydroxy ester 6 was reduced to hydroxy aldehyde 7 using i-$Bu_2AlH$ and a procedure identical to that described later for the synthesis of compound 10. A 60% overall yield from compound 4 was achieved.

Synthesis of Compound 8

Hydroxy aldehyde 7 was subjected to the Wittig reaction as described at Chapleo, C.B.; Finch, M.A.W.; Lec, T.V.; Roberts, S.M. *J. Chem. Soc. Perkin I,* 1980, 2084 and later for the synthesis of compound 11, and the desired acid 8 was obtained in 62% yield.

Synthesis of Hydroxy Ester 9

A generally known procedure described at Yankee, E.W.; Axen, v. Bundy, G.L. *J. Am. Chem. Soc.* 1974, 96, 5869, was followed. Compound 4 (0.22 g, 0.72 mmol) was taken up in 37 ml of dry THF and cooled to −78° C. To this was added 3.77 ml (15.75 equiv) of 3.0 M MeMgBr in diethyl ether. The reaction was stirred at −78° C. for four hours. The reaction was then quenched with 10 ml of saturated ammonium chloride solution and allowed to warm up to room temperature. After adding an additional 25 ml of saturated ammonium chloride solution, the reaction mixture was extracted with ether. The ether layer was washed with saturated sodium chloride solution, dried over $Na_2SO_4$, and the solvent removed under vacuum. Column chromatography of the resulting residue using 1:1 hexane/ethyl acetate as the eluant yielded 137 mg (59% yield) of compound 9.

Synthesis of Hydroxy Aldehyde 10

Ester 9 (137 mg, 0.425 mmol) was taken up in 28 ml of methylene chloride and cooled to −78° C. This solution was treated with 1.4 ml of 1 M i-Bu$_2$AlH in methylene chloride (3.3 equiv) and stirred for three hours at −78° C. The reaction mixture was then quenched with 1 ml of methanol and treated with 3 ml of saturated ammonium chloride solution. The reaction mixture was then warmed to room temperature, diluted with ether, washed with saturated ammonium chloride solution, dried over $Na_2SO_4$, and the solvent removed under vacuum. Flash column chromatography of the resulting residue yielded 106 mg (90% yield) of the desired hydroxy aldehyde 10.

Synthesis of Compound 11

The Wittig reaction was employed as described at Chapleo, C.B.; Finch, M.A.W.; Lec, T.V.; Roberts, S.M. *J. Chem. Soc., Perkin I* 1980, 2084. (4-Carboxybutyl)triphenylphosphonium bromide (0.70 g, 1.58 mmol) was suspended in 6 ml of THF under a nitrogen atmosphere. Potassium t-butoxide (0.36 g, 3.2 mmol) was added and the orange colored mixture was stirred for 15 minutes at room temperature. Then hydroxy aldehyde 10 (0.11 g, 0.395 mmol) in 3.8 ml of THF was added, and the reaction mixture was stirred at room temperature for three hours. Sulfuric acid (40 ml of 2 N) and water were added and the product was extracted with ether, washed with 2 N sulfuric acid and water, and dried over $MgSO_4$. The residue obtained after evaporation of the solvent was chromatographed using 2:1 hexane/ethyl acetate plus a few drops of acetic acid to yield 77 mg (54% yield) of compound 11.

What is claimed is:

1. A process for making prostaglandin precursors, comprising:
    reacting a norbornene type compound selected from the group consisting of norbornene, substituted norbornene compounds and norbornene related bicyclic olefins, with an alkyl (acetoxymercurio) carboxylate, where said alkyl is $C_1$ to $C_8$ in the presence of a polar organic solvent insert to the reactants, and in the presence of a palladium salt and a 1-alken-3-one where said alken-one is $C_3$ to $C_{12}$ to provide a keto ester of bicycloheptane.

2. The process of claim 1, wherein said alkyl (acetoxymercurio) carboxylate is ethyl (acetoxymercurio) acetate.

3. The process of claim 2, wherein said ethyl (acetoxymercurio) acetate is produced from 1,1-difluoroethylene.

4. The process of claim 1, wherein said norbornene type compound is norbornene.

5. The process of claim 1, wherein said palladium salt is a palladium halide salt.

6. The process of claim 5, wherein said palladium salt is dilithium tetrachloropalladate.

7. The process of claim 2, wherein said 1-alken-3-one is 1-octen-3-one.

* * * * *